4/10/84 OR 4,441,503

128/660

United States Patent [19]

O'Donnell

[11] 4,441,503

[45] Apr. 10, 1984

[54] COLLIMATION OF ULTRASONIC LINEAR ARRAY TRANSDUCER

[75] Inventor: Matthew O'Donnell, Schenectady, N.Y.

[73] Assignee: General Electric Company, Schenectady, N.Y.

[21] Appl. No.: 340,140

[22] Filed: Jan. 18, 1982

[51] Int. Cl.[3] ........................ A61B 10/00; H01L 41/22

[52] U.S. Cl. ........................ 128/660; 310/336; 73/644

[58] Field of Search ........................ 128/660-663; 73/632, 642, 644; 310/334-337

[56] References Cited

U.S. PATENT DOCUMENTS

| | | | |
|---|---|---|---|
| 3,971,962 | 7/1976 | Green | 73/642 X |
| 4,197,921 | 4/1980 | Alphonse et al. | 73/642 X |
| 4,211,948 | 7/1980 | Smith et al. | 310/322 |
| 4,211,949 | 7/1980 | Brisken et al. | 73/642 X |
| 4,361,044 | 11/1982 | Kupperman et al. | 73/642 X |
| 4,385,255 | 5/1983 | Yamaguchi et al. | 128/660 X |

*Primary Examiner*—Kyle L. Howell
*Assistant Examiner*—Francis J. Jaworski
*Attorney, Agent, or Firm*—Donald R. Campbell; James C. Davis, Jr.; Paul R. Webb, II

[57] ABSTRACT

The beam characteristics of individual array elements of a linear transducer array are altered by collimation of ultrasonic waves using critical angle effects. A phased array transducer for a medical imaging system with a 90° image sensor has a collimator which is a thin sheet of polyethylene. Acoustic waves whose angle of incidence is greater than the critical angle are totally reflected. Insignificant ultrasonic energy is generated outside of the imaged sector and there is a modest insertion loss over the acceptance region.

5 Claims, 7 Drawing Figures

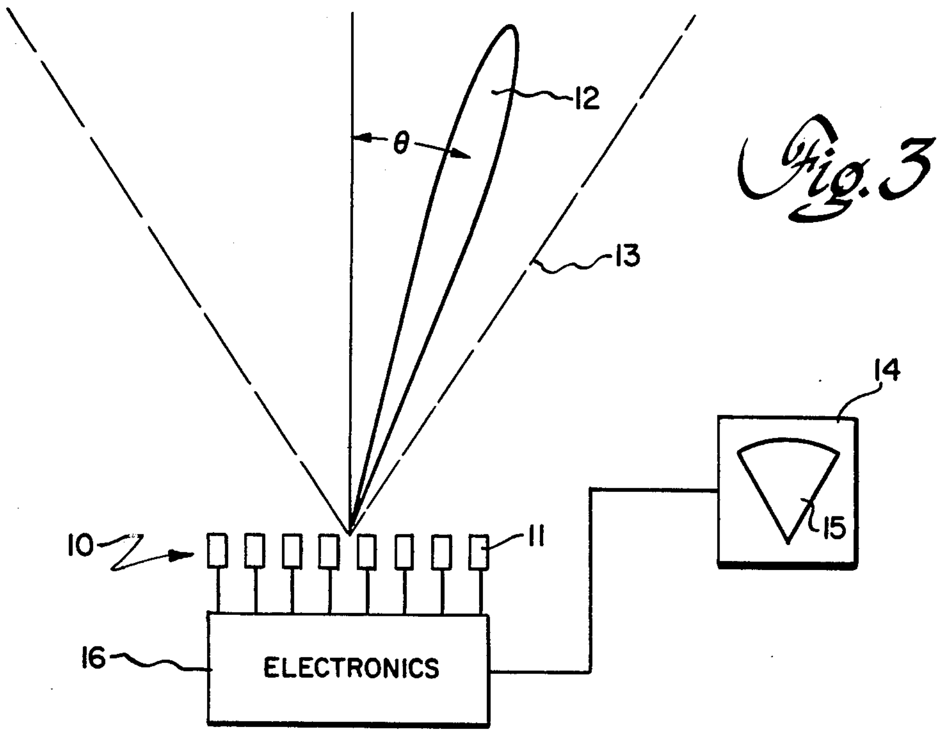
Fig. 3
Fig. 4a
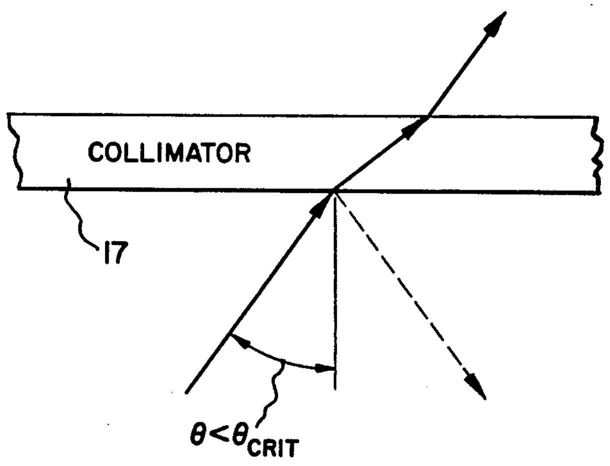
Fig. 4b
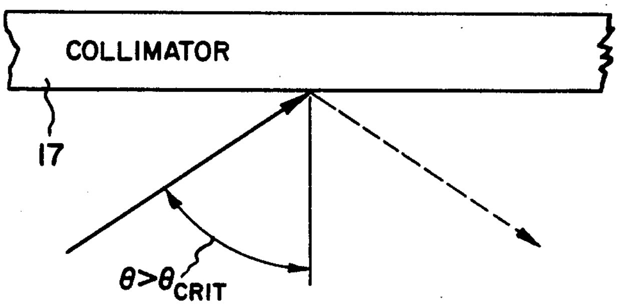

COLLIMATION OF ULTRASONIC LINEAR ARRAY TRANSDUCER

BACKGROUND OF THE INVENTION

This invention relates to improving the beam pattern of linear array transducers used in ultrasonic imaging systems.

Ultrasonic phased array sector scanners require a wide angular view, typically ±45°, for medical diagnostic and clinical applications. To meet this requirement, ultrasonic arrays are constructed from a large number of elements each of which exhibits a wide acceptance angle. The beam pattern for an individual array element which represents the ideal for imaging applications (see FIG. 1) is such that the beam is of uniform amplitude over the acceptance region and is zero outside this region. In practice, the ideal pattern is approximated by the diffraction pattern from a radiator (element) of dimension comparable to an ultrasonic wavelength. A typical beam pattern of an actual, practical array element (FIG. 2) exhibits the desirable feature that the amplitude is nearly uniform up to approximately 40°, but also has the undesirable feature that significant energy is directed outside the nominal acceptance region.

Substantial effort has been directed toward developing ultrasonic arrays whose elements exhibit beam patterns which approach the ideal pattern of FIG. 1. However, previous work in tailoring the beam pattern from individual array elements has focused on altering parameters which influence the diffraction patterns.

SUMMARY OF THE INVENTION

Improved ultrasonic linear arrays are realized whose elements exhibit the desired angular resonse and approach the ideal beam properties. Collimation via critical angle effects is used to change the beam characteristics of individual array elements. The generation of significant ultrasonic energy outside the designated acceptance region is eliminated, while not altering significantly the beam characteristics within the acceptance region. The illustrative embodiment is a phased array transducer in a sector scan imaging system which performs wide angle (90°) sector scans. The transducer array has a collimator in the form of a sheet of polyethylene approximately one wavelength in thickness at the lowest useful emission frequency. Acoustic waves whose angle of incidence is less than the critical angle (47°-55° for human tissue) are transmitted and waves whose angle of incidence is greater than the critical angle are totally reflected. The angular range of transmitted waves is equal to or greater than the angular extent of the sector of the body which is scanned and imaged by the system. The critical angle is approximately equal to the maximum scan angle of the imager.

BRIEF DESCRIPTION OF THE DRAWINGS

FIG. 3 is a simplified diagram of a phased array sector scanner;

FIG. 4*a* and 4*b* illustrate transmission of an acoustic wave by the collimator and total reflection when incident at an angle greater than the critical angle;

DESCRIPTION OF THE PREFERRED EMBODIMENTS

Figure 1:
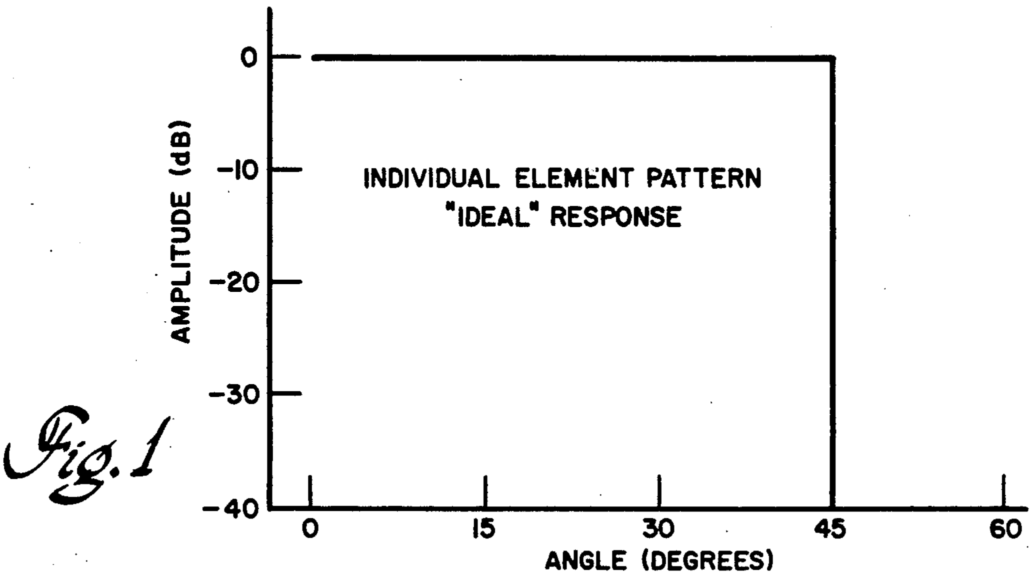
FIG. 1 shows one half of the beam pattern of an ideal array element.

Collimation of ultrasonic waves affords an independent technique for tailoring the ultrasonic beam used in imaging systems where the characteristics of the beam are determined primarily by diffraction effects. Consequently, collimation can be used to eliminate some of the undesirable features of ultrasonic beams generated by diffraction. The specific technique utilizes thin sheets of polyethylene to limit the acceptance angle of phased array sector scanners used in medical imaging to approximately a ±50° sector while exhibiting a modest insertion loss over the acceptance region.

The real time, sector scan imaging system illustrated in simplified form in FIG. 3 is described in detail in U.S. Pat. No. 4,155,260 and other patents assigned to this assignee. Linear transducer array 10 is comprised of a large number of piezoelectric transducer elements 11 which are energized by excitation pulses in a linear time sequence to form an ultrasound beam 12 and direct the beam in a preselected azimuth direction to transmit a pulse of ultrasound. In order to steer the beam electronically to an angle $\theta$ from the normal to the array at the sector origin point, a time delay increment is added successively to each transducer excitation signal as one moves down the array from one end to the other to compensate for propagation path time differences. By progressively changing the time delay between successive excitation pulses, the angle on one side of the normal is changed by increments, and to form an acoustic beam at the other side of the normal, the timing of the excitation pulses is reversed. The total sector scan angle indicated by dashed lines 13 is approximately 90°. The display device 14 for the 90° image sector 15 is typically a cathode ray tube. The transmitting and receiving channels and other imager electronics is indicated generally as 16.

Each transducer element 11 is an omnidirectional device and radiates sound to every point in the object. The ultrasonic energy outside the 90° sector that is scanned and imaged can produce artifacts in the image because echoes reflected by object features outside the 90° sector may be received by the transducer elements. The beam pattern of a practical array device was discussed with regard to FIG. 2. It may be made flat over the image sector, so as to approach the ideal beam pattern in FIG. 1, by compensating in the electronics, adding gain where the amplitude is down. However, the electronics cannot compensate for energy outside the maximum scan angle from the normal of 45°. The improved phased array transducer with a collimator eliminates the generation of significant ultrasonic energy outside the ±45° acceptance region, and does not significantly change the beam characteristics within the acceptance region.

The basic principle of collimation via critical angle effects is illustrated in FIGS. 4*a* and 4*b*. If the incident wave impinges on the collimator 17 at an angle $\theta$ less than the critical angle $\theta_{crit}$, as depicted in FIG. 4*a*, then the wave is transmitted through the collimating material. In contrast, if the incidence wave impinges on the collimating material at an angle greater than the critical angle, as shown in FIG. 4*b*, then the incident wave is totally reflected, and no energy is transmitted through the collimator. Thus, this simple method based on critical angle effects passes signals within a certain angular range and rejects signals outside that range.

To implement the concept, materials are found which exhibit simple critical angle effects, and exhibit minimal losses over the acceptance region. In general, simple critical angle effects for longitudinal waves can be obtained only if the material used for the collimator does not support shear waves. in the absence of shear waves, the critical angle is given by the expression $$\theta_{crit} = \arc\sin\left(\frac{C_1}{C_2}\right) \quad (1)$$

wherein $C_1$ is the longitudinal wave sound velocity in the object, such as the human body, and $C_2$ is the longitudinal wave sound velocity in the collimator. The velocity of sound of the collimator must be chosen so that the critical angle is slightly larger than the acceptance region, the $\pm 45°$ sector, of the imaging system. Thus, the material chosen for collimation cannot support shear waves, and for medical applications the longitudinal wave sound velocity results in a critical angle of approximately 50°. Polyethylene is a solid which weakly supports a shear wave, and has a longitudinal wave sound velocity of about 1950 meters/sec. Consequently, polyethylene approximates the simple critical angle properties shown in FIGS. 4a and 4b, with a critical angle between 47° and 55° for human tissue.

Although polyethylene exhibits the appropriate properties for the collimation of ultrasonic transducers used in real time phased array imaging systems, it is a very lossy material. Further, the arrival time of transmitted pulses of ultrasound may be different. To minimize losses over the acceptance region and in order to not change the arrival time, thin layers of polyethylene are used. However, if the layers are made too thin, then they will not exhibit critical angle effects. The plate is approximately one wavelength thick at the lowest useful emission frequency of the transducer to insure that the polyethylene acts as a collimator. For example, if the lowest frequency to be collimated is 1 MHz, then a half wavelength plate is about 40 mils thick. If the lowest frequency to be collimated is 2 MHz, then a half wavelength plate is about 20 mils thick. For these thicknesses, critical angle effects will collimate the beam desired, but the two-way insertion loss will be only 3–5 dB over the acceptance region.

An imaging system which performs, say, a 60° sector scan has a collimator made of a different material. Knowing that the longitudinal sound velocity in tissue is 1500–1600 meters/sec., and that the critical angle is equal to at least the maximum scan angle of 30° or a little larger, the solution of equation (1) gives $C_2$, the longitudinal wave sound velocity in the collimator. An appropriate material is then selected.

Figure 2:
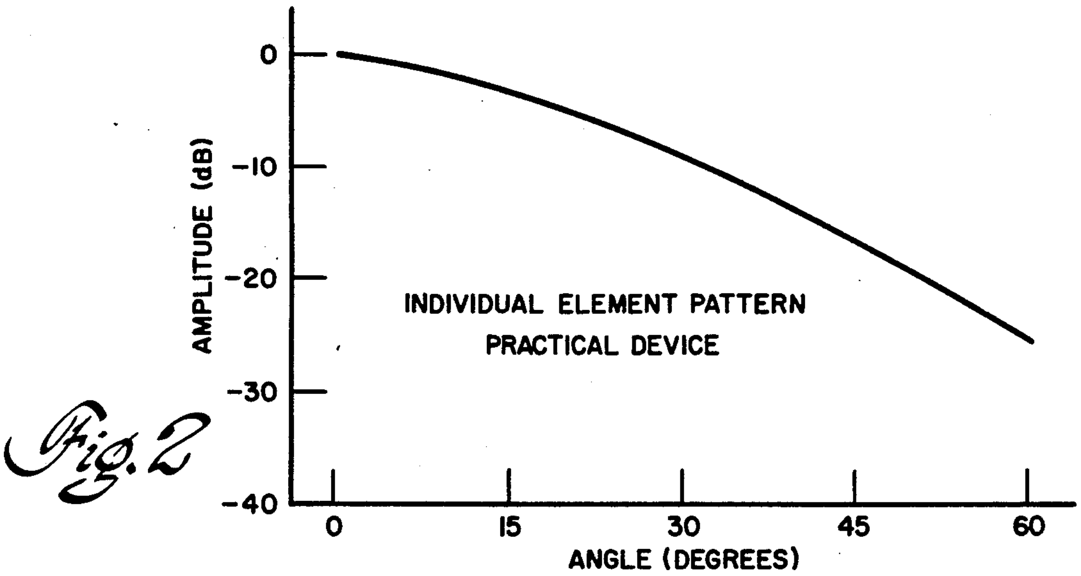
FIG. 2 shows one half of the beam pattern of a practical array element that has been constructed.
Figure 5:
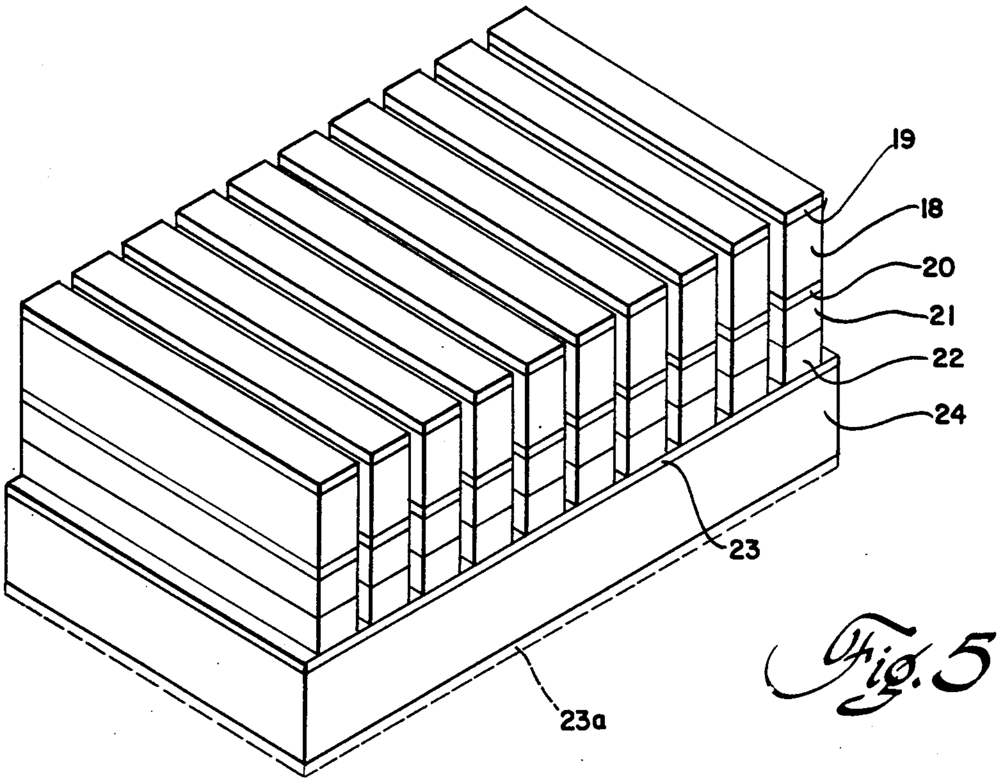
FIG. 5 is a perspective view of a transducer array which has a thin sheet collimator.

FIG. 5 illustrates the preferred embodiment of the improved phased array transducer, which has a collimator and whose elements exhibit the desired angular response so as to closely approximate the ideal beam properties presented in FIG. 1. The array itself is described in detail in U.S. Pat. No. 4,211,948, L. S. Smith and A. F. Brisken, assigned to the same assignee, the disclosure which is incorporated herein by reference. This array has high sensitivity and a wide field of view. It is comprised of a large number of piezoelectric transducer elements 18 which have electrodes 19 and 20 on opposite faces and a width on the order of one wavelength at the emission frequency. Fully cut through quarter-wave impedance matching layers 21 and 22, of Pyrex ® and Plexiglas ®, are attached to each element. The collimator 23, a continuous thin sheet of polyethylene, is adjacent to the front surfaces of the second matching layer and is covered by the wear plate 24. Alternatively, the collimating sheet 23a (shown in dashed lines) is adhered to the front surface of the wear plate. The wear plate is made of material, such as filled silicon rubber, in which the longitudinal sound velocity is equal to or less than that in the human body and in which the acoustic impedance for longitudinal sound waves is approximately equal to that of the body.

This phased array transducer transmits pulses of ultrasound at many different scan angles so as to scan a full 90° sector of the human body. Ultrasonic waves generated by every transducer element 18 are guided through impedance matching layers 21 and 22 and impinge on collimator 23. Acoustic waves whose angle of incidence is less than the critical angle (about 50°) are transmitted through the collimator and wear plate, and acoustic waves whose angle of incidence is greater than the critical angle are totally reflected. Insignificant ultrasonic energy is generated outside of the $\pm 45°$ sector which is scanned and imaged, and beam characteristics within the scanned sector are not altered. Image quality is improved because there is no image "clutter" from outside the sector.

Figure 6:
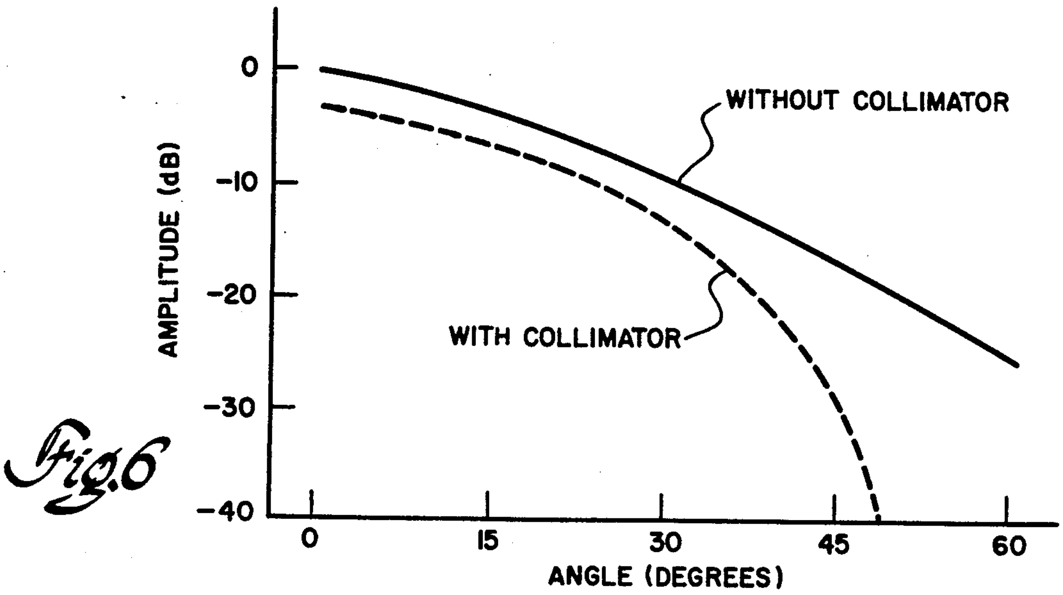
FIG. 6 shows the measured individual element beam pattern with and without a polyethylene collimator.

In FIG. 6, the results of measurements which demonstrate the practical application of a polyethylene collimator are presented. The solid curve represents the beam profile measured on an element of an array which was constructed. The dashed curve represents the results of measurements obtained on the same array element after a 40 mil thick polyethylene plate was bonded to the front of the wear plate on the transducer. The polyethylene plate acted as a collimator, restricting the acceptance region to about $\pm 45°$. The plate introduced a two-way insertion loss of only 3 db over the acceptance region.

Raster linear arrays are also improved by the addition of a collimator.

While the invention has been particularly shown and described with reference to preferred embodiments thereof, it should be understood by those skilled in the art that various changes in form and details may be made therein without departing from the spirit and scope of the invention.

What is claimed is:

1. An improved ultrasonic transducer for an imaging system comprising:

a linear array of transducer elements which generates beams of ultrasound and scans a sector of an object;

said transducer having, in front of said array, a continuous collimating layer which exhibits critical angle effects and transmits to the object acoustic waves incident at an angle less than the critical angle and totally reflects acoustic waves incident at a greater angle, the angular range of transmitted waves corresponding approximately to the angular extent of the scanned sector;

said collimating layer being made of a material that supports longitudinal waves and does not substantially support shear waves, and is approximately one wavelength thick at the known lowest useful emission frequency of said transducer.

2. The ultrasonic transducer of claim 1 wherein said material is polyethylene.

3. An improved ultrasonic phased array transducer for a sector scan imaging system comprising:

a linear transducer array which transmits pulses of ultrasound at many scan angles to scan a sector of the human body and is comprised of a plurality of transducer elements each of which generates ultrasonic waves and to which are attached fully cut through impedance matching layers, a wear plate covering said elements and matching layers; and a continuous collimator plate adjacent to said wear plate which exhibits critical angle effects and transmits and totally reflects ultrasonic waves emitted by every element whose angle of incidence of respectively less than and greater than the critical angle, said critical angle being approximately equal to the maximum scan angle;

whereby insignificant ultrasonic energy is generated outside of the sector scanned and imaged by the system.

4. The ultrasonic transducer of claim 3 wherein said collimator plate has a thickness of approximately one wavelength at the known lowest useful emission frequency of said transducer.

5. The ultrasonic transducer of claim 4 wherein said collimator plate is polyethylene.

* * * * *